(12) United States Patent
Motohara et al.

(10) Patent No.: US 8,294,817 B2
(45) Date of Patent: Oct. 23, 2012

(54) IMAGE PICKUP MODULE HAVING GUIDE MEMEBER FOR MECHANICAL STRENGTH

(75) Inventors: Hiroyuki Motohara, Hachioji (JP); Yoshiro Nishimura, Okaya (JP)

(73) Assignee: Olympus Corporation, Tokyo (JP)

( * ) Notice: Subject to any disclaimer, the term of this patent is extended or adjusted under 35 U.S.C. 154(b) by 104 days.

(21) Appl. No.: 12/850,983

(22) Filed: Aug. 5, 2010

(65) Prior Publication Data
US 2010/0321565 A1 Dec. 23, 2010

Related U.S. Application Data
(63) Continuation of application No. PCT/JP2009/050813, filed on Jan. 21, 2009.

(30) Foreign Application Priority Data

Feb. 7, 2008 (JP) ................................. 2008-027577

(51) Int. Cl.
*H04N 5/225* (2006.01)
*H04N 9/04* (2006.01)
*A61B 1/04* (2006.01)
*A61B 1/00* (2006.01)

(52) U.S. Cl. .......... 348/375; 348/45; 348/340; 600/101; 600/109; 257/432

(58) Field of Classification Search .................. 348/372, 348/373, 374, 207.99, 45, 65, 72, 74, 75, 348/76, 375, 340; 600/101, 109, 112; 257/432–434
See application file for complete search history.

(56) References Cited

U.S. PATENT DOCUMENTS
6,142,930 A 11/2000 Ito et al.

FOREIGN PATENT DOCUMENTS

| | | | |
|---|---|---|---|
| JP | 10-033470 A | | 2/1998 |
| JP | 2000-201884 | | 7/2000 |
| JP | 2001-094843 A | | 4/2001 |
| JP | 3417777 | | 4/2003 |
| JP | 2004-121750 | | 4/2004 |
| JP | 2004121750 A | * | 4/2004 |
| JP | 2005-074035 A | | 3/2005 |
| JP | 2006-270568 | | 10/2006 |
| JP | 2006270568 A | * | 10/2006 |

OTHER PUBLICATIONS

Abstract of Japanese Patent Publication No. 10-192236, dated Jul. 28, 1998.
International Search Report dated Mar. 24, 2009.
International Preliminary Report on Patentability together with the Written Opinion dated Sep. 7, 2010.

* cited by examiner

*Primary Examiner* — Jason Whipkey
*Assistant Examiner* — Marly Camargo
(74) *Attorney, Agent, or Firm* — Scully, Scott, Murphy & Presser, P.C.

(57) ABSTRACT

There is provided an image pickup module which can be formed by a simple process while securing the mechanical strength of an inner lead at the time of bending and when fixed, without increasing an outer dimension of the image pickup module.

The image pickup module includes an image pickup element having an image pickup surface, and a flexible substrate is drawn to be directed rearward of the image pickup surface. A guide member which fixes the image pickup element and the flexible substrate is provided, and the guide member includes a portion which is extended along a rear surface of the image pickup element, and a portion which is extended along a gap between the image pickup element and the flexible substrate.

3 Claims, 9 Drawing Sheets

IMAGE PICKUP MODULE HAVING GUIDE MEMEBER FOR MECHANICAL STRENGTH

CROSS-REFERENCE TO RELATED APPLICATION

The present application is based upon and claims the benefit of priority from the prior Japanese Patent Application No. 2008-027577 filed on Feb. 7, 2008; the entire contents of which are incorporated herein by reference.

TECHNICAL FIELD

The present invention relates to an image pickup module in which, a flexible substrate is connected to an image pickup element.

BACKGROUND ART

As a conventional image pickup module in which, a flexible substrate is connected to an image pickup element, for example, an image pickup module which is installed in an electronic endoscope described in Patent Literature 1 (Japanese Patent No. 3417777 Specification) can be cited. In the image pickup module disclosed in Patent Literature 1, an electrical insulating member is applied or an electrical insulating member in the form of a sheet is laminated on a surface of an inner lead at a side along the image pickup element. Accordingly, an electrical insulation between a side surface of the image pickup element and the inner lead is secured, and furthermore, an outer dimension of an assembly of a unit of the image pickup element and a flexible substrate has been made smaller.

Patent Literature: Japanese Patent No. 3417777 Specification

DISCLOSURE OF THE INVENTION

Problems to be Solved by the Invention

However, in the image pickup module described in Patent Literature 1, it has been difficult to say that strength of a bent portion of the inner lead in particular, is sufficiently secured.

The present invention has been made in view of the abovementioned circumstances, and a flexible substrate on which, a protective layer having a mechanical strength is formed on both surfaces in advance, and a guide member which fixes the flexible substrate to the image pickup element and has a guiding function at the time of bending the flexible substrate are provided. Accordingly, an object of the present invention is to provide an image pickup module which can be formed by a simple process while securing the mechanical strength of the inner lead at the time of bending and when fixed, without increasing the outer dimension of the image pickup module.

Means for Solving the Problems

To solve the abovementioned problems and to achieve the object, an image pickup module according to the present invention includes an image pickup element having an image pickup surface, and a flexible substrate is drawn to be directed rearward of the image pickup surface, and a guide member which fixes the image pickup element and the flexible substrate is provided, and the guide member includes a portion which is extended along a rear surface of the image pickup element, and a portion which is extended along a gap between the image pickup element and the flexible substrate.

In the image pickup module according to the present invention, it is preferable that electronic components are mounted on the flexible substrate.

In the image pickup module according to the present invention, it is preferable that the guide member is formed by a plurality of members.

In the image pickup module according to the present invention, in the guide member, the portion which is extended along the rear surface of the image pickup element can be disposed along the entire rear surface of the image pickup element.

In the image pickup module according to the present invention, in the guide member, the portion which is extended along the rear surface of the image pickup element can be disposed along an angular portion formed by at least the image pickup element and the flexible substrate.

In the image pickup module according to the present invention, it is preferable that in the guide member, an inclination is provided to a surface toward the flexible substrate which is extended from the image pickup element.

Effects of the Invention

An image pickup module according to the present invention includes an image pickup element having an image pickup surface, and a flexible substrate is drawn to be directed rearward of the image pickup surface. A guide member which fixes the image pickup element and the flexible substrate is provided, and since the guide member includes a portion which is extended along a rear surface of the image pickup element, and a portion which is extended along a gap between the image pickup element and the flexible substrate, it is possible to form an image pickup module having a small size with a simple structure, as well as high mechanical strength.

Moreover, since electronic components are mounted on the flexible substrate, increased functionality of the image pickup module becomes possible, and it is possible to provide an image pickup module having a high added-value to a user.

Furthermore, the guide member being formed by the plurality of members, it is possible to design such that, strength of fixing of the image pickup element and the flexible substrate is enhanced, and to design such that the yield of the image pickup module is improved.

Moreover, in the guide member, by disposing the portion which is extended along the rear surface of the image pickup element along the entire rear surface of the image pickup element, it is possible to enhance the strength of fixing of the image pickup element and the flexible substrate.

Furthermore, in the guide member, when the portion which is extended along the rear surface of the image pickup element is disposed along the angular portion formed by at least the image pickup element and the flexible substrate, it is possible to make small a volume occupied by the guide member in the image pickup module, and a degree of freedom of designing of the image pickup module is extended.

Moreover, in the guide member, as the inclination is provided to the surface toward the flexible substrate which is drawn from the image pickup element, it is possible to make small a volume occupied by the guide member in the image pickup module without making small a contact area of the guide member and the flexible substrate, and accordingly, a small-sizing of the image pickup module becomes possible, and the degree of freedom of designing of the image pickup module is extended.

DESCRIPTION OF REFERENCE NUMERALS 1 image pickup element
1a rear surface
2 image pickup surface
3 bump
4 inner lead
5 adhesive
6 guide member
6a guide portion
6b guide portion
7a protective layer
7b protective layer
8 flexible substrate
10 adhesive
10A image pickup module
11a electronic component
12 cable
12a electronic component
20A image pickup module
30A image pickup module
361 guide member
361a guide surface
361b guide surface
362 guide member
362a guide portion
362b guide portion
40A image pickup module
461 guide member
461a guide surface
461b guide surface
462 guide member
462a guide portion
462b guide portion
50A image pickup module
56 guide member
56a guide portion
56b guide portion
60A image pickup module
661 guide member
661a guide surface
661b guide surface
662 guide member
662a guide portion
662b guide portion
70A image pickup module
761 guide member
761a guide surface
761b guide surface
762 guide member
762a guide portion
762b guide portion
80A image pickup module
86 guide member
86a guide portion
86b guide portion

BEST MODE FOR CARRYING OUT THE INVENTION

Embodiments of an image pickup module according to the present invention will be described below in detail by referring to the accompanying diagrams. However, the present invention is not restricted to the embodiments described below.

First Embodiment

Figure 1:
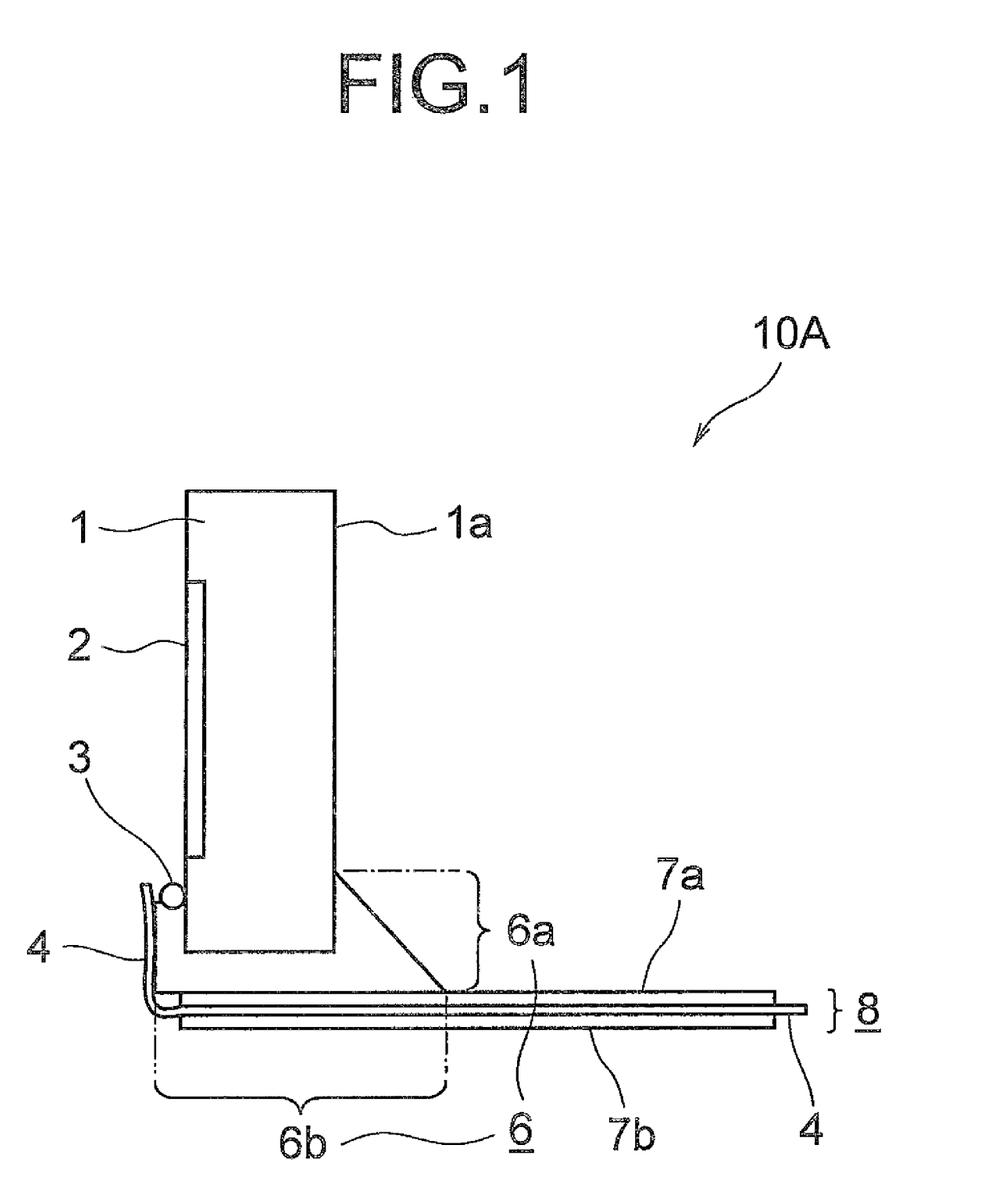
FIG. 1 is a side view showing a structure of an image pickup module according to a first embodiment.
Figure 2:
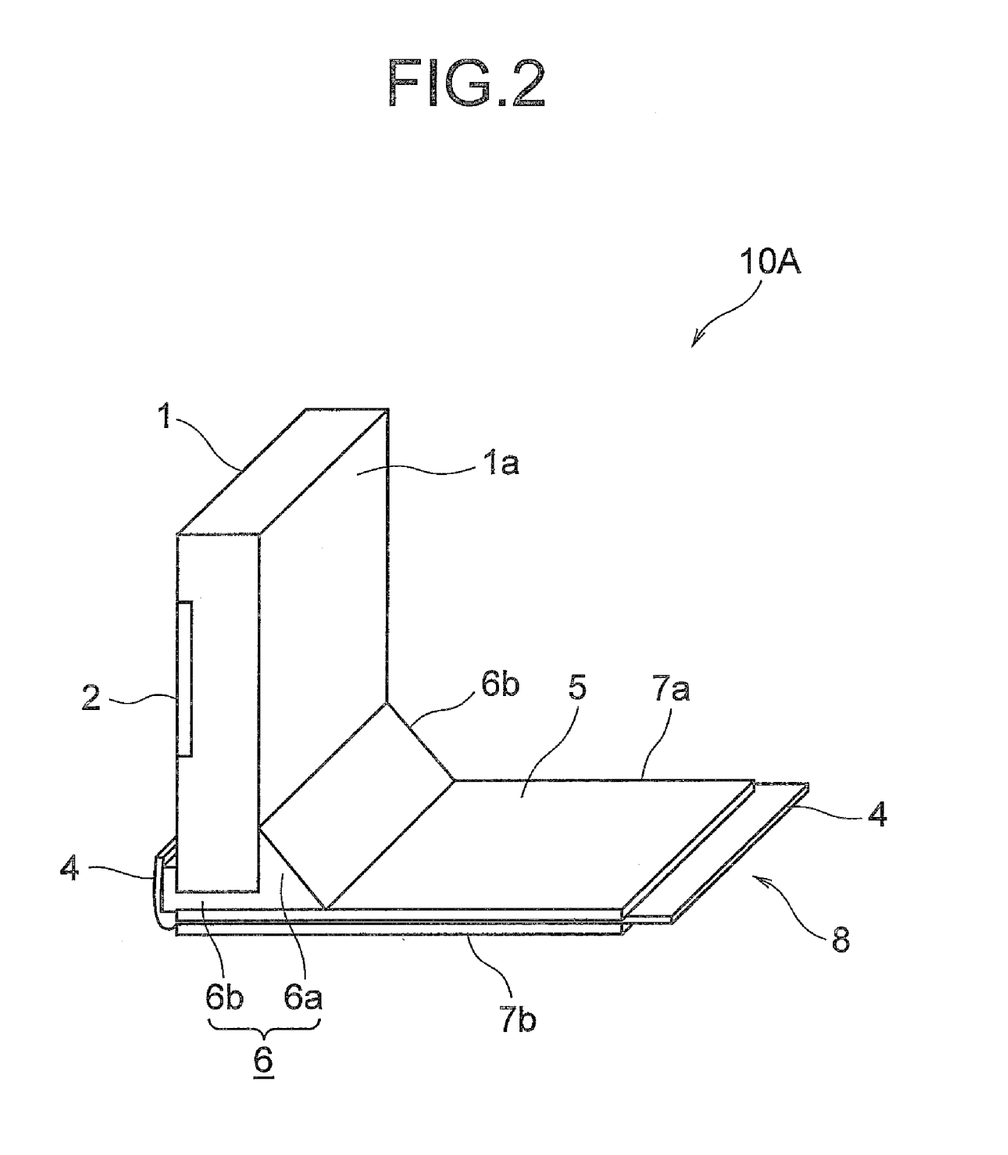
FIG. 2 is perspective view showing the structure of the image pickup module according to the first embodiment.

In FIG. 1, an image pickup module 10A according to a first embodiment is shown. Moreover, a perspective view of FIG. 1 is shown in FIG. 2. A structure of the image pickup module 10A is as follows.

An electrode (not shown in the diagram) for driving an image pickup element 1, and an electrode (not shown in the diagram) for outputting a video signal from the image pickup element 1 are provided on an image pickup surface 2 of the image pickup element 1, and a bump 3 is formed on these electrodes.

A flexible substrate 8 (such as a TAB circuit member) is formed by protective layers 7a and 7b, and an inner lead 4 (such as a TAB lead). The inner lead 4 has at least a portion of an upper surface and a lower surface covered by the protective layers 7a and 7b respectively in advance and therefore has mechanical strength. It desirable that the protective layers 7a and 7b are formed of a material such as polyimide, and have mechanical strength, flexibility, heat resisting property, and insulating property. Moreover, even a combined substrate in which these members are combined may serve the purpose.

A guide member 6 has a guide portion 6a which is extended along a surface of the image pickup element 1 (a rear surface of the image pickup element 1a), on an opposite side of the image pickup surface 2, and a guide portion 6b which is extended along a gap between the image pickup element 1 and the flexible substrate 8. The guide portion 6a of the guide member 6, which is extended along the surface of the image pickup element 1 at the opposite side of the image pickup surface 2 is disposed to be along an angular portion formed by the rear surface 1a of the image pickup element 1 and the flexible substrate 8 (the protective layer 7a).

A manufacturing process of the image pickup module 10A is as described in (1), (2), and (3) below.

(1) The flexible substrate 8 having the guide member 6, the image pickup element 1, and the inner lead 4 covered by the protective layers 7a and 7b is set on an image pickup module manufacturing jig.

(2) The image pickup element 1 and the flexible substrate 8 are fixed by the guide member 6.

(3) The inner lead 4 of the flexible substrate 8 is disposed upon bending along a partial surface of the guide member 6.

It is preferable that a material of the guide member 6 is a material which enables to fix the image pickup element 1 and the flexible substrate 8, as well as a part of the flexible substrate 8 is bent along the surface of the guide member 6, and an adhesive 5 which is curable by heat and ultraviolet light can be used.

Moreover, the flexible substrate 8 is connected to each electrode of the image pickup element 1 by the bump 3, and a signal which drives the image pickup element 1 and a video signal which is output from the image pickup element 1 are transmitted by the inner lead 4.

Strength of fixing of the image pickup element 1 and the flexible substrate 8 may be enhanced further by applying more adhesive to an area surrounded by a front surface of the image pickup element 1, the bump, and the inner lead 4.

According to the abovementioned structure, it is possible to form the image pickup module 10A by a simple structure while securing mechanical strength at the time of bending the inner lead 4 and when the inner lead 4 is fixed, without increasing an outer dimension of the image pickup module 10A. Consequently, it is possible to realize further small-sizing of the image pickup module 10A.

Second Embodiment

Figure 3:
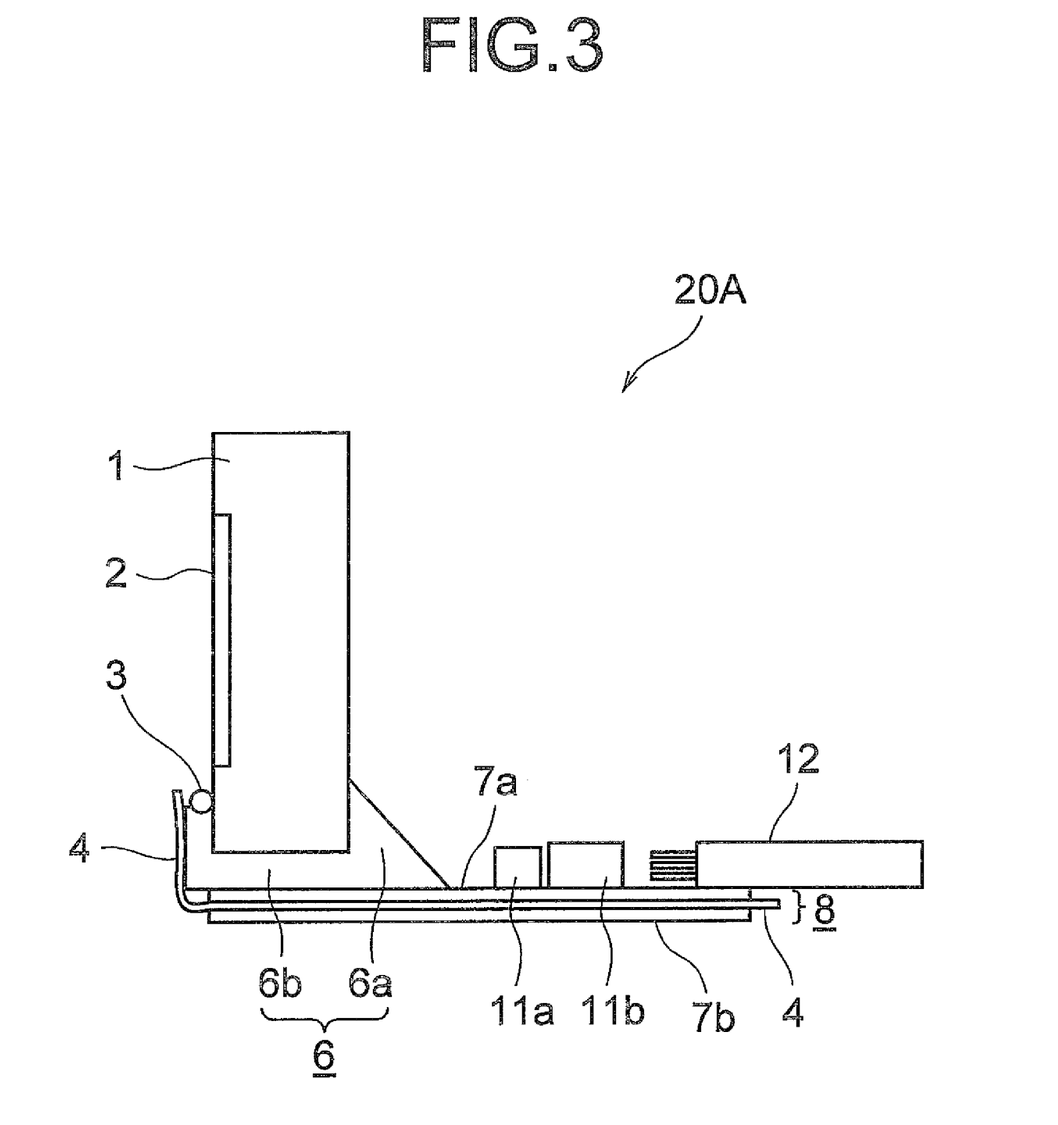
FIG. 3 is a side view showing a structure of an image pickup module according to a second embodiment.

Next, an image pickup module 20A according to a second embodiment will be described while referring to FIG. 3. Here, FIG. 3 is a side view showing a structure of the image pickup module 20A according to the second embodiment.

The image pickup module 20A according to the second embodiment, as compared with the image pickup module 10A according to the first embodiment, differs at a point that electronic components 11a and 12a, and a cable 12 are mounted on the flexible substrate 8. In the image pickup module 20A according to the second embodiment, it is possible to enhance further the strength of fixing the image pickup element 1 and the flexible substrate 8 by applying more adhesive in an area surrounded by the front surface of the image pickup element 1, the bump 3, and the inner lead 4. Moreover, as electronic components 11a and 12a, an IC in which, components such as a resistance, a condenser, and a transistor are integrated can be cited as examples.

According to the image pickup module 20A according to the second embodiment, since an increased functionality of the image pickup module becomes possible, it is possible to provide to a user an image pickup module having a high added-value.

Third Embodiment

Figure 4:
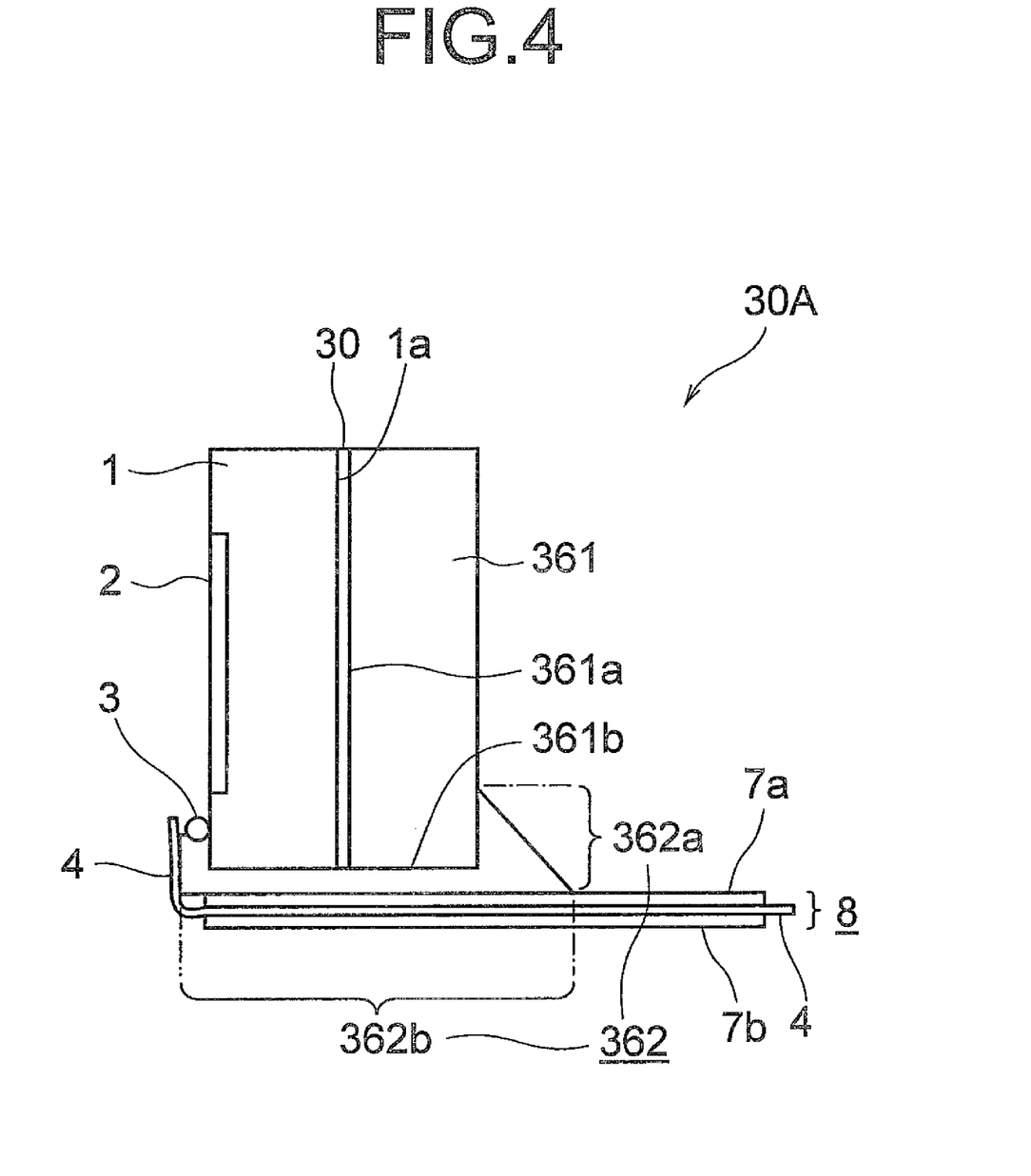
FIG. 4 is a side view showing a structure of an image pickup module according to a third embodiment.

Next, an image pickup module 30A according to a third embodiment will be described while referring to FIG. 4. Here, FIG. 4 is a side view showing a structure of the image pickup module 30A according to the third embodiment.

The image pickup module 30A according to the third embodiment, as compared with the image pickup modules 10A and 20A according to the first embodiment and the second embodiment, differs at a point that the guide member is formed by two members, or in other words, a guide member 361 and a guide member 362. The guide member 361 has a guide surface 361a which is extended along an entire rear surface 1a of the image pickup element 1 (a surface of the image pickup element 1 at an opposite side of the image pickup surface 2), and a guide surface 361b which is extended along the flexible substrate 8 (the protective layer 7a). Moreover, the guide member 362 has a guide portion 362a which is extended along a surface of the guide member 361, at an opposite side of the guide surface 361a, and a guide portion 362b which extended along a gap between the guide surface 361b of the guide member 361 and the image pickup element 1, and the flexible substrate 8 (the protective layer 7a).

Moreover, in the image pickup module 30A according to the third embodiment, firstly, the guide member 361 is fixed by an adhesive 30 to the surface 1a of the image pickup element 1, at an opposite side of the image pickup surface 2. The guide member 361 can be formed by an organic substrate, a ceramic substrate, a glass substrate, or, a combined substrate of these substrates. Moreover, it is desirable that the guide member 361 is installed by a bonding apparatus which is capable of installing upon positioning accurately. The rest of the structure and manufacturing process are similar to the image pickup module 10A according to the first embodiment.

The strength of fixing of the image pickup element 1 and the flexible substrate 8 may be enhanced further by applying more adhesive to an area surrounded by the front surface of the image pickup element 1 and the inner lead 4. Moreover, the electronic components 11a and 12a, and the cable 12 may be mounted on the flexible substrate 8.

According to the image pickup module 30A according to the third embodiment, it is possible to enhance the strength of fixing of the image pickup element and the flexible substrate, and the yield of the image pickup module is improved, and it is possible to provide a low-price image pickup module to the user.

Fourth Embodiment

Figure 5:
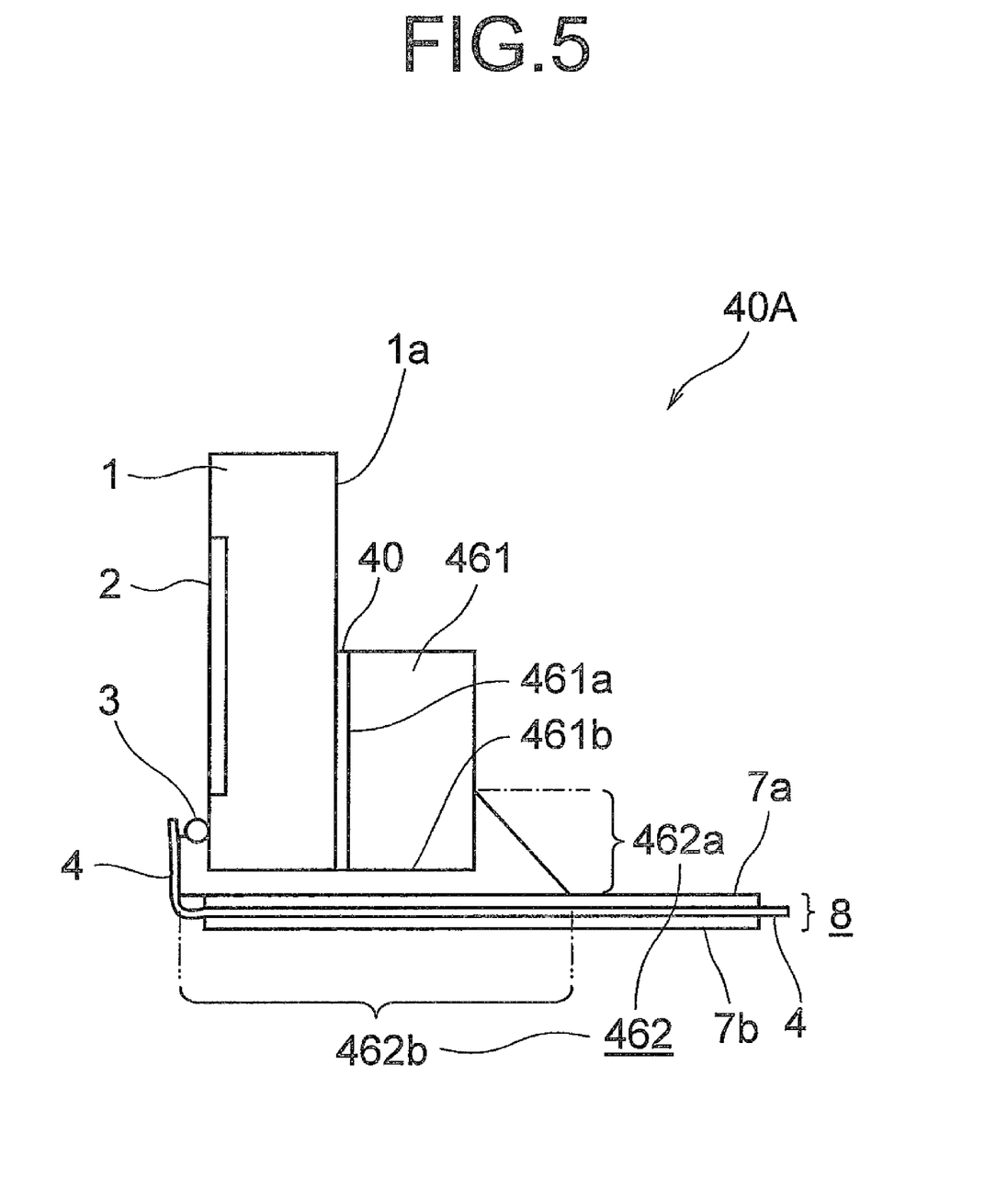
FIG. 5 is a side view showing a structure of an image pickup module according to a fourth embodiment.

Next, an image pickup module 40A according to a fourth embodiment will be described by referring to FIG. 5. FIG. 5 is a side view showing a structure of the image pickup module 40A according to the fourth embodiment.

The image pickup module 40A according to the fourth embodiment, as compared with the image pickup modules 10A, 20A, and 30A according to the first embodiment, the second embodiment, and the third embodiment, differs at a point that the guide member which is extended along the surface of the image pickup element 1, at an opposite side of the image pickup surface is provided to be along an angular portion formed by the rear surface 1a of the image pickup element 1 and the flexible substrate 8 (the protective layer 7a).

The guide member in the image pickup module 40A according to the fourth embodiment is formed by a guide member 461 and a guide member 462. The guide member 461 has a guide surface 461a which is extended along the rear surface 1a of the image pickup element 1, at an angular portion formed by the rear surface 1a of the image pickup element 1 (the surface of the image pickup element 1 at an opposite side of the image pickup surface 2) and the flexible substrate 8 (the protective layer 7a), and a guide surface 461b which is extended along the flexible substrate 8. Moreover, the guide member 462 has a guide portion 462a which is extended along a surface of the guide member 461, at an opposite side of the guide surface 461a, and a guide portion 462b which is extended along a gap between the guide surface 461b of the guide member 461 and the image pickup element 1, and the flexible substrate 8 (the protective layer 7a).

In the image pickup module 40A according to the fourth embodiment, firstly, the guide member 461 smaller than the image pickup element 1 is fixed by an adhesive 40 to the surface of the image pickup element 1, at the opposite side of the image pickup surface 2. The rest of the structure and manufacturing process are similar to the second embodiment.

The strength of fixing of the image pickup element 1 and the flexible substrate 8 may be enhanced by applying more adhesive to an area surrounded by the front surface of the image pickup element 1, the bump 3, and the inner lead 4. Moreover, the electronic components 11a and 12a, and the cable 12 may be mounted on the flexible substrate 8.

According to the image pickup module 40A according to the fourth embodiment, it is possible to make small a volume occupied by the guide member 46 in the image pickup module, and accordingly, the small-sizing of the image pickup module becomes possible, and a degree of freedom of designing of the image pickup module is extended.

Fifth Embodiment

Next, an image pickup module 50A according to a fifth embodiment will be described while referring to FIG. 6. The image pickup module 50A according to the fifth embodiment, as compared with the image pickup modules 10A, 20A, 30A, and 40A according to the embodiments from the first embodiment to the fourth embodiment differs at a point that an inclined surface is provided to a guide portion 56a. In other words, in the image pickup modules 10A, 20A, 30A, and 40A according to the embodiments from the first embodiment to the fourth embodiment, a flat surface formed by the flexible substrate 8 has been disposed to be substantially orthogonal to the rear surface 1a of the image pickup element 1, whereas, in the image pickup module according to the fifth embodiment, an angle formed by the flat surface formed by the flexible substrate 8 and the rear surface 1a of the image pickup element 1 is smaller than 90 degrees.

Figure 6:
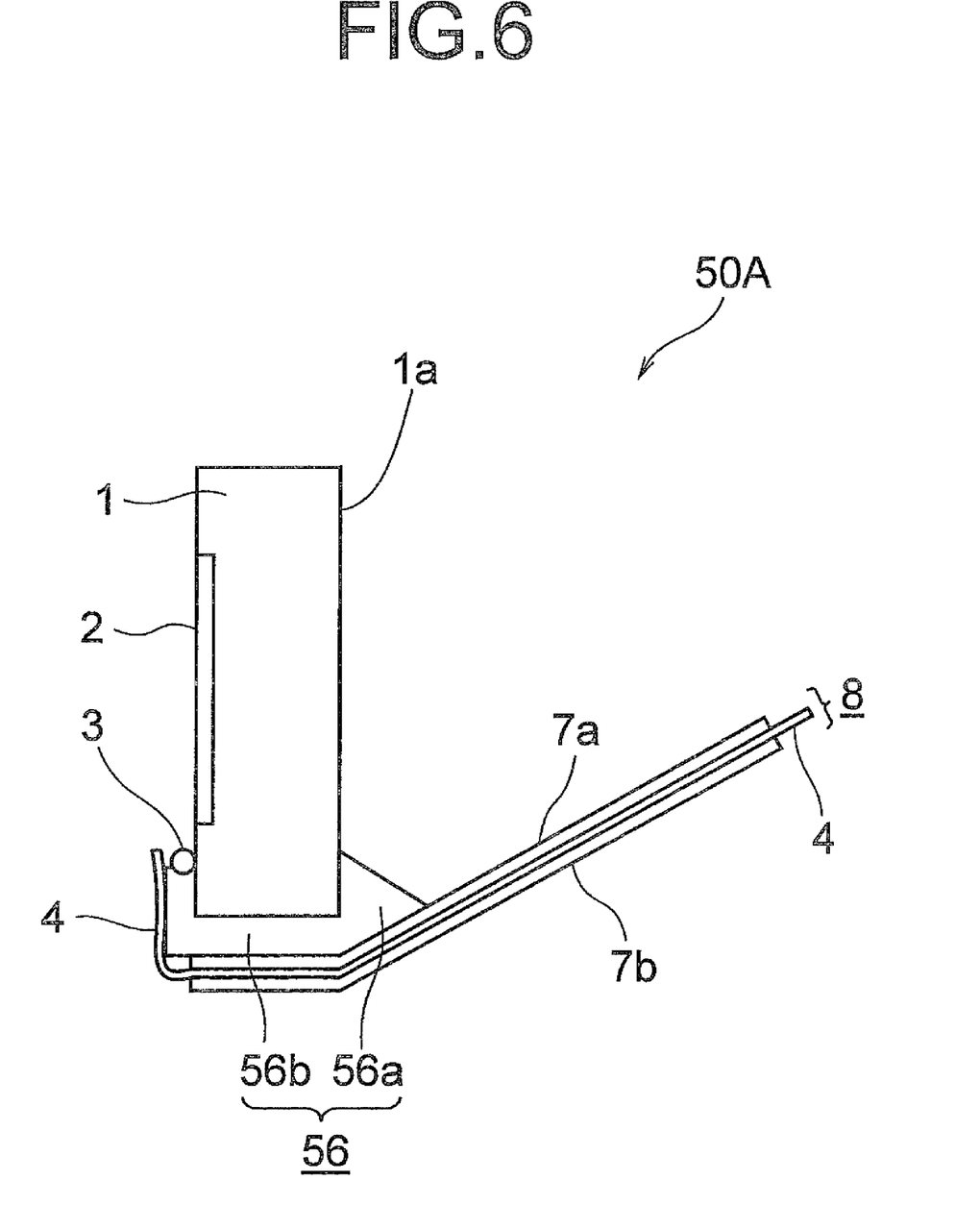
FIG. 6 is a side view showing a structure of an image pickup module according to a fifth embodiment.

As shown in FIG. 6, a guide member 56 according to the fifth embodiment includes a guide portion 56a which is extended along the rear surface 1a of the image pickup element 1, and a guide portion 56b which is extended along a gap between the image pickup element 1 and the flexible substrate 8. The guide portion 56a of the guide member 56, which is extended along the rear surface 1a of the image pickup element 1, has a shape that enables to support such that the flexible substrate 8 is at less than 90 degrees with respect to the rear surface 1a of the image pickup element 1. Here, FIG. 6 is a side view showing a structure of the image pickup module according to the fifth embodiment.

Figure 7:
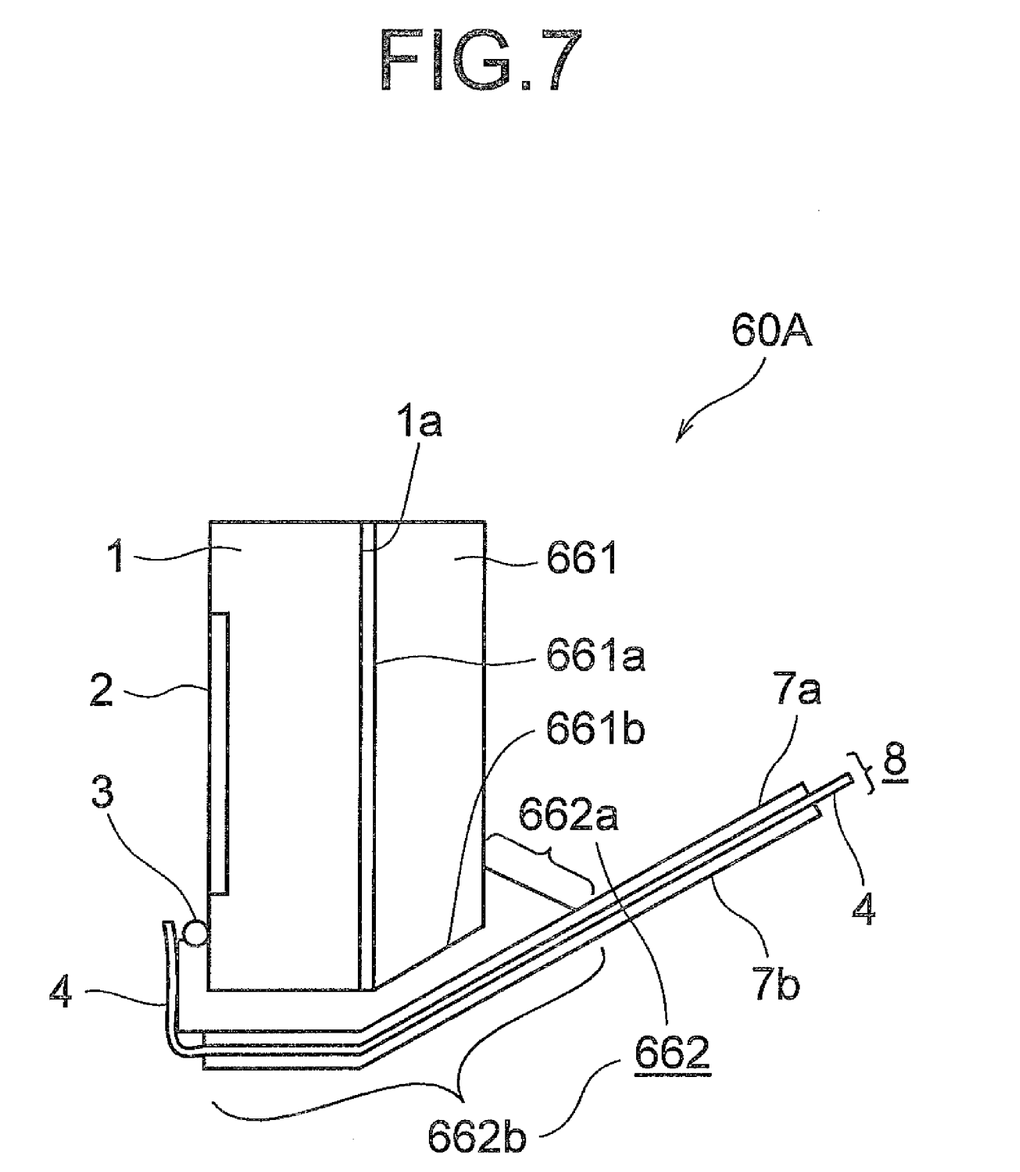
FIG. 7 is a side view showing a structure of an image pickup module according to a modified embodiment of the fifth embodiment.

However, instead of the guide member 56, a guide member as in an image pickup module 60A shown in FIG. 7 can also be used. This guide member is formed by a guide member 661 and a guide member 662. The guide member 661 has a guide surface 661a which is extended along the rear surface 1a of the image pickup element 1 (the surface of the image pickup element 1, at an opposite side of the image pickup surface 2), and a guide surface 661b which is extended along the flexible substrate 8 (the protective layer 7a). Moreover, the guide member 662 has a guide portion 662a which is extended along a surface of the guide member 661 at an opposite side of the guide surface 661a, and a guide portion 662b which is extended along a gap between the guide surface 661b of the guide member 661 and the image pickup element 1, and the flexible substrate 8 (the protective layer 7a). Here, FIG. 7 is a side view showing a structure of the image pickup module 60A according to a modified embodiment of the fifth embodiment.

Figure 8:
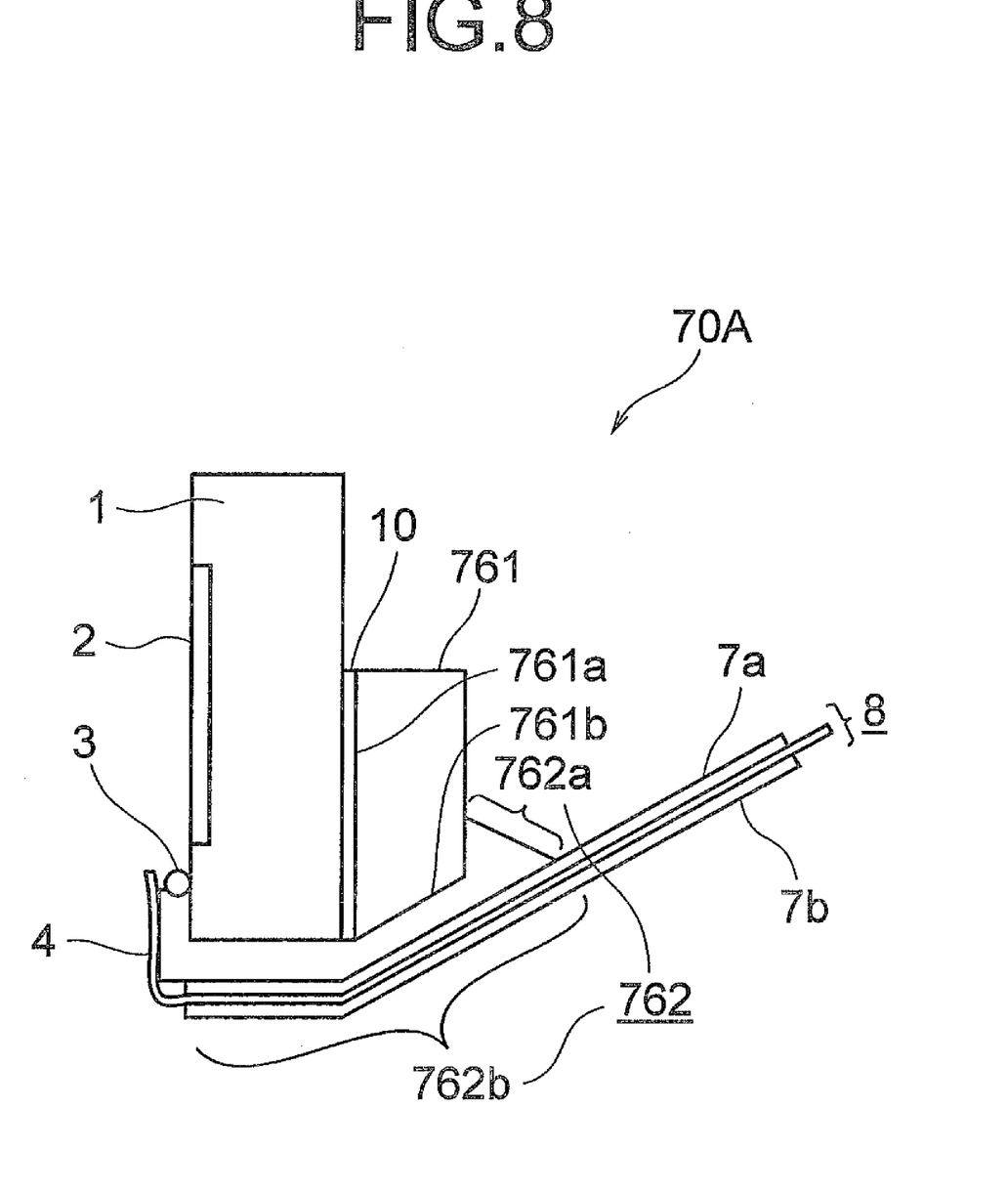
FIG. 8 is a side view showing a structure of an image pickup module according to another modified embodiment of the fifth embodiment.

Moreover, instead of the guide member 56, a guide member as in an image pickup module 70A shown in FIG. 8 can also be used. This guide member is formed by a guide member 761 and a guide member 762. The guide member 761 has a guide surface 761a which is extended along the rear surface 1a of the image pickup element, at an angular portion formed by the rear surface 1a of the image pickup element 1 (the surface of the image pickup element 1 at the opposite side of the image pickup surface 2) and the flexible substrate 8 (the protective layer 7a), and a guide surface 761b which is extended along the flexible substrate 8. Moreover, the guide member 762 has a guide portion 762a which is extended along a surface of the guide member 761 at an opposite side of the guide surface 761a, and a guide portion 762b which is extended along a gap between the guide surface 761b of the guide member 761a and the image pickup element 1, and the flexible substrate 8 (the protective layer 7a). FIG. 8 is a side view showing a structure of the image pickup module 70A according to another modified embodiment of the fifth embodiment.

Figure 9:
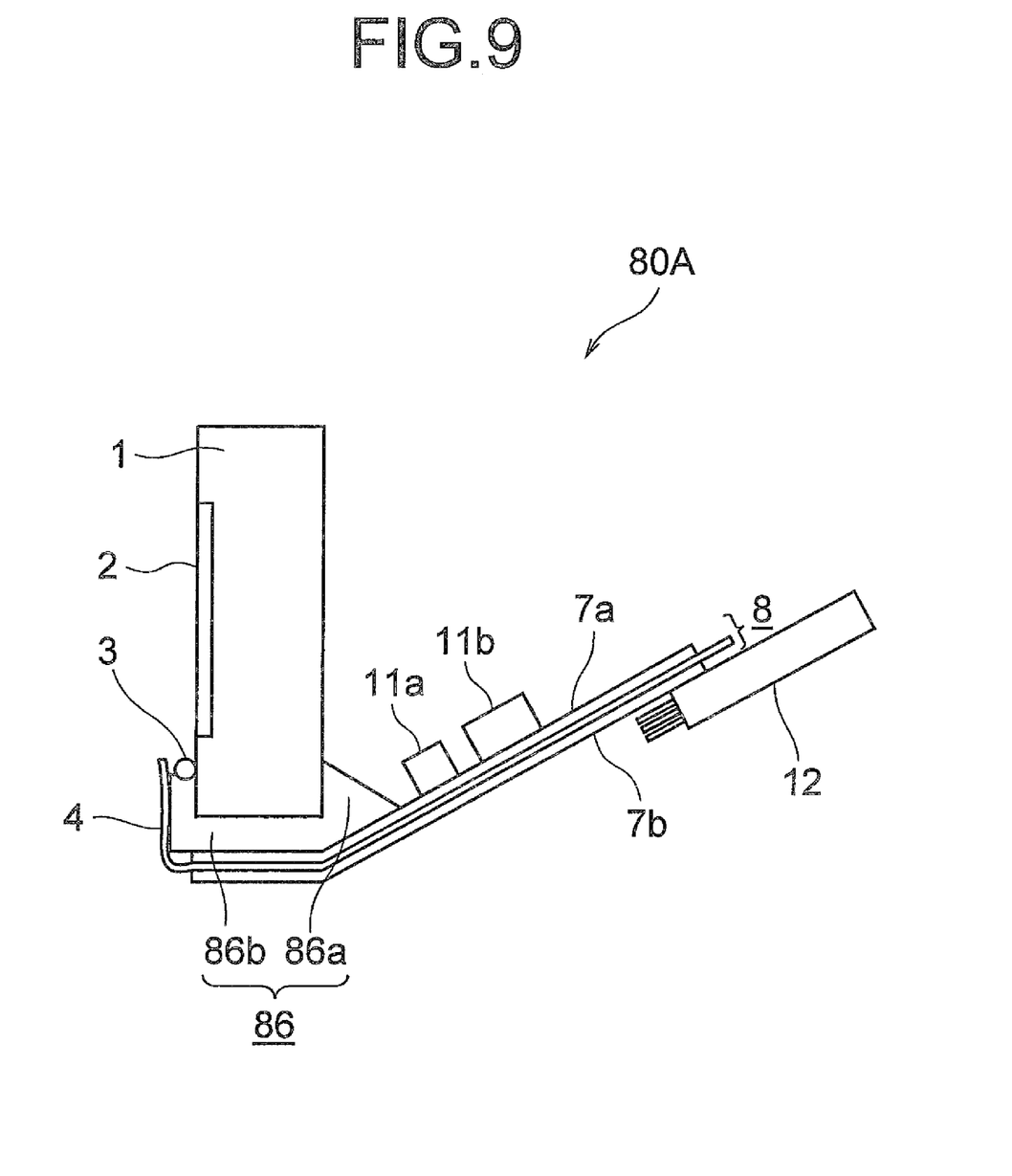
FIG. 9 is a side view showing a structure of an image pickup module according to still another modified embodiment of the fifth embodiment.

Moreover, the electronic components 11a and 12a, and the cable 12 can be mounted on the flexible substrate 8. Furthermore, for making small the volume of the image pickup module, the electronic components 11a and 12a, and the cable 12 may be mounted partly on a front surface and partly on a rear surface of the flexible substrate 8. Here, FIG. 9 is a side view showing a structure of an image pickup module according to still another modified embodiment of the fifth embodiment. A guide member 86 includes a guide portion 86a which is extended along the rear surface 1a of the image pickup element 1, and a guide portion 86b which is extended along a gap between the image pickup element 1 and the flexible substrate 8. The guide portion 86a of the guide member 86, which is extended along the rear surface 1a of the image pickup element 1 has a shape that enables to support such that the flexible substrate 8 is at less than 90 degrees with respect to the rear surface 1a of the image pickup element 1.

According to the image pickup modules according to the fifth embodiment and the modified embodiments thereof, as it is possible to provide an inclination to the flexible substrate 8, it is possible to make small a volume occupied by the guide member 6 in the image pickup module without making small an area of contact of the guide member and the flexible substrate 8. Accordingly, it is possible to realize small-sizing of the image pickup module, and the degree of freedom of designing of the image pickup module is extended.

INDUSTRIAL APPLICABILITY

As it has been described above, the image pickup module according to the present invention is useful for an image pickup module which is built-in in a small-size apparatus, and is suitable for an image pickup module which is built-in in an endoscope apparatus in particular.

The invention claimed is:
1. An image pickup module comprising:
an image pickup element having an image pickup surface;
a flexible substrate which is disposed to be directed rearward of the image pickup surface; and
first and second guide members which fix the image pickup element and the flexible substrate;
wherein the first guide member includes a first guide surface which is extended along a surface opposite to the image pickup surface of the image pickup element, and a second guide surface which is extended along the flexible substrate, and
wherein the second guide member includes a first guide portion which is extended along a surface opposite to the first guide surface of the first guide member, and a second guide portion which is extended along a portion between the second guide surface and the flexible substrate.

2. The image pickup module according to claim 1, wherein the first guide surface of the first guide member is extended along a whole area of the surface opposite to the image pickup surface of the image pickup.

3. The image pickup module according to claim 1, wherein the first guide member is one or more of an organic substrate, a ceramic substrate, and a glass substrate, which is fixed by an adhesive, on the surface opposite to the image pickup surface of the image pickup element.

* * * * *

UNITED STATES PATENT AND TRADEMARK OFFICE
CERTIFICATE OF CORRECTION

| | |
|---|---|
| PATENT NO. | : 8,294,817 B2 |
| APPLICATION NO. | : 12/850983 |
| DATED | : October 23, 2012 |
| INVENTOR(S) | : Hiroyuki Motohara et al. |

It is certified that error appears in the above-identified patent and that said Letters Patent is hereby corrected as shown below:

On the Title page item (54) and in the specification, col. 1, line 1 should read:

IMAGE PICKUP MODULE HAVING GUIDE MEMBER FOR MECHANICAL STRENGTH

Signed and Sealed this
Ninth Day of April, 2013

Teresa Stanek Rea
*Acting Director of the United States Patent and Trademark Office*